United States Patent [19]

Hammen

[11] 4,100,347
[45] Jul. 11, 1978

[54] 3,4-DIHYDRO-2-METHYL-4-OXO-2H-1,2-BENZOTHIAZINE-3-CARBOXYLIC ACID-1,1-DIOXIDE

[75] Inventor: Philip D. Hammen, East Lyme, Conn.

[73] Assignee: Pfizer Inc., New York, N.Y.

[21] Appl. No.: 694,572

[22] Filed: Jun. 10, 1976

[51] Int. Cl.² .................................. C07D 279/02
[52] U.S. Cl. .............................. 544/49; 424/246
[58] Field of Search .................. 260/243 R; 544/49

[56] References Cited

U.S. PATENT DOCUMENTS

| | | | |
|---|---|---|---|
| 3,492,298 | 1/1970 | Rasmussen | 260/243 |
| 3,591,584 | 7/1971 | Lombardino | 260/243 |
| 3,808,205 | 4/1974 | Sircar et al. | 260/243 |
| 3,892,740 | 7/1975 | Lombardino | 260/243 |

OTHER PUBLICATIONS

Lombardino et al., J. Heterocyclic Chem., vol. 13, pp. 333–335 (1976).

*Primary Examiner*—John M. Ford
*Attorney, Agent, or Firm*—Connolly and Hutz

[57] ABSTRACT

Process for production of 3,4-dihydro-2-methyl-4-oxo-2H-1,2-benzothiazine-3-carboxylic acid-1,1-dioxide by hydrolysis, in the presence of hydroxide ions, of an alkyl or aralkyl ester thereof followed by precipitation of the acid at pH below 6.0 and its use as an intermediate for the production of N-(2-pyridyl)-3,4-dihydro-2-methyl-4-oxo-2H-1,2-benzothiazine-3-carboxamide-1,1-dioxide and the analogous N-(2-thiazolyl)-compound, effective antiinflammatory agents.

1 Claim, No Drawings

3,4-DIHYDRO-2-METHYL-4-OXO-2H-1,2-BENZO-THIAZINE-3-CARBOXYLIC ACID-1,1-DIOXIDE

BACKGROUND OF THE INVENTION

1. Field of the Invention

This invention relates to a process for producing 3,4-dihydro-2-methyl-4-oxo-2H-1,2-benzothiazine-3-carboxylic acid-1,1-dioxide, a valuable intermediate for the synthesis of non-steroidal antiinflammatory agents. More particularly, it relates to the preparation of said carboxylic acid compound by base hydrolysis of alkyl or aralkyl esters of 3,4-dihydro-2-methyl-4-oxo-2H-1,2-benzothiazine-3-carboxylic acid-1,1-dioxide and to the use of the acid for production of the antiinflammatory agents N-(2-pyridyl)-3,4-dihydro-2-methyl-4-oxo-2H-1,2-benzothiazine-3-carboxamide-1,1-dioxide and N-(2-thiazolyl)-3,4-dihydro-2-methyl-4-oxo-2H-1,2-benzothiazine-3-carboxamide-1,1-dioxide.

2. Description of the Prior Art

The instability of β-keto carboxylic acids, evidenced by their tendency to undergo decarboxylation, is well known to those skilled in the art. U.S. Pat. No. 3,892,740, issued July 1, 1975, and *J. Heterocyclic Chem.,* 13, 333 (1976) report that 3,4-dihydro-4-oxo-2H-1,2-benzothiazine-3-carboxylic acid-1,1-dioxides have been prepared by hydrolysis of the corresponding ester but they decarboxylate rapidly once formed. The observed instability arises from their β-keto structure.

The preparation of N-substituted-3,4-dihydro-4-oxo-2H-1,2-benzothiazine-3-carboxamide-1,1-dioxides useful as antiinflammatory agents is described in U.S. Pat. Nos. 3,591,584; 3,891,637 and 3,892,740, issued July 6, 1971; June 24, 1975 and July 1, 1975, respectively.

The first patent discloses two routes for the synthesis of N-substituted-benzothiazine-carboxamide-1,1-dioxides: (a) reaction of the appropriate 3,4-dihydro-4-oxo-2H-1,2-benzothiazine-1,1-dioxide with an organic isocyanate; and (b) ammonolysis of an ester of 3,4-dihydro-4-oxo-2H-1,2-benzothiazine-3-carboxylic acid-1,1-dioxide with ammonia or an appropriate amine. The second patent describes the preparation of such compounds wherein the N-substituent is a heterocyclic moiety by a transamidation reaction. The third patent reports preparation of such carboxamide derivatives by contacting a 3,4-dihydro-4-alkoxy-2H-1,2-benzothiazine-3-carboxylic acid-1,1-dioxide with a coupling promoter (dicyclohexylcarbodiimide, $POCl_3$, N-ethoxycarbonyl-2-ethoxy-1,2-dihydroquinoline) followed by contacting the resulting carboxamide with a mineral acid to convert the 4-alkoxy group to 4-oxo.

In each instance, the particular synthetic route employed carefully avoided the formation of a 3,4-dihydro-4-oxo-2H-1,2-benzothiazine-3-carboxylic acid-1,1-dioxide, even as a transient intermediate, in order to circumvent the heretofore reported instability of the β-keto function of such acids. This reported instability of such acids is in keeping with the well-known tendency of β-keto acids to undergo decarboxylation.

SUMMARY OF THE INVENTION

It has now been unexpectedly and surprisingly found that 3,4-dihydro-2-methyl-4-oxo-2H-1,2-benzothiazine-3-carboxylic acid-1,1-dioxide (formula I) can be prepared and isolated as a crystalline compound, stable at ambient temperatures, by hydrolysis of an ester thereof in the presence of a source of hydroxide ion, followed by acidification of the reaction mixture to pH below 6.0.

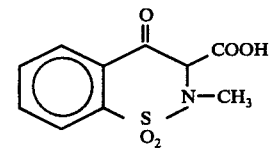

(I)

The acid thus produced is a valuable intermediate for the preparation of non-steroidal antiinflammatory agents such as those having formula II by acylation of the appropriate amine.

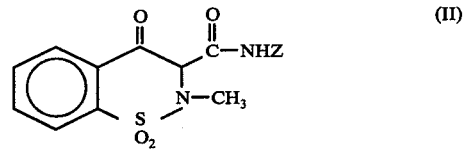

(II)

In formula II, Z is selected from the group consisting of 2-pyridyl and 2-thiazolyl.

DETAILED DESCRIPTION OF THE INVENTION

The process of this invention for producing 3,4-dihydro-2-methyl-4-oxo-2H-1,2-benzothiazine-3-carboxylic acid-1,1-dioxide comprises hydrolysis, in the presence of a source of hydroxide ion, of a compound having formula III

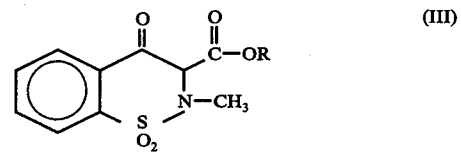

(III)

wherein R is selected from the group consisting of alkyl having from one to twelve carbon atoms and phenylalkyl having up to three carbon atoms in the alkyl moiety, followed by acidification of the reaction mixture to afford the compound of formula I.

Compounds having structures I, II and III exist as mixtures of keto and enol tautomers, as is taught in U.S. Pat. No. 3,892,740. Formulae I, II and III depict the keto tautomers. It is intended to embrace both tautomers of the compounds described herein within the scope of this invention. For convenience only the keto forms are illustrated.

The 3,4-dihydro-2-methyl-4-oxo-2H-1,2-benzothiazine-3-carboxylic acid-1,1-dioxide esters are prepared according to the procedure described in U.S. Pat. No. 3,591,584. The alkyl esters having from one to four carbon atoms and especially the methyl and ethyl esters are favored as reactants in the hydrolysis process because of their ease of preparation.

The hydrolysis of formula III esters is accomplished in the presence of hydroxide ions using as source of hydroxide ion metal hydroxides, such as the alkali metal hydroxides and the alkaline earth metal hydroxides. The hydrolysis can be conducted in aqueous or non-aqueous solvent systems. When conducted in an aqueous solvent system, the hydrolysis is carried out at temperatures from 20° C. to the reflux temperature of the reaction medium. Of the metal hydroxides, alkali metal hydroxides are favored—indeed, preferred—because of their greater water solubility relative to that of the alkaline earth metal hydroxides. The preferred alkali metal hydroxides are sodium and potassium hydroxides because of their availability and, as regards large scale production, their more favorable economics relative to that of other alkali metal hydroxides.

The favored alkaline earth metal hydroxides are calcium and magnesium hydroxides because of their cost and availability relative to that of other alkaline earth metal hydroxides.

In addition to metal hydroxides, quaternary ammonium hydroxides such as tetraalkyl ammonium hydroxides, trialkyl benzyl ammonium hydroxides and dialkyl dibenzyl ammonium hydroxides wherein the alkyl groups have from one to twelve carbon atoms can be used as sources of hydroxide ion. Representative of such bases are tetramethyl ammonium hydroxide, dimethyl dibenzyl ammonium hydroxide and trimethyl benzyl ammonium hydroxide.

The molar ratio of metal hydroxide to ester reactant is not critical but can vary from about 1:1 to about 10:1. In actual practice, molar ratios of from about 1:1 to about 5:1 have been found effective in achieving satisfactory rate and yield of hydrolysis.

When conducted in a non-aqueous solvent system, the same metal hydroxides as are enumerated above can serve as source of hydroxide ion. In order to achieve efficient reaction, use is made of the solubilizing effect afforded by the presence of a crown ether; that is, a macrocyclic ether, on the metal hydroxide in hydrocarbon solvents such as benzene or toluene. Representative of crown ethers useful in this process are 18-crown-6, dibenzo-18-crown-6, cyclohexyl-18-crown-6, dicyclohexyl-18-crown-6 and cyclohexyl-15-crown-5. The favored hydroxide ion sources for use in non-aqueous solvent systems are the alkali metal hydroxides because of the relatively strong tendency of crown ethers to complex the alkali metal cation, their ease of solubilization and enhanced reactivity in the presence of crown ethers. The preferred alkali metal hydroxides are potassium and sodium hydroxides.

This method, hydrolysis in a non-aqueous system with the assistance of a crown ether, is the preferred hydrolysis method since it affords substantial yields of the desired 3,4-dihydro-2-methyl-4-oxo-2H-1,2-benzothiazine-3-carboxylic acid-1,1-dioxide.

In general, when using crown ethers, the molar ratio of alkali metal or alkaline earth hydroxide to crown ether and ester reactant can vary from about 1:0.1:1 to about 100:1:10. In actual practice, an excess of the metal hydroxide is used since it tends to minimize the reaction time and afford more complete hydrolysis of the ester than does lesser amounts of metal hydroxide. Larger proportions of crown ether can, of course, be used. The reaction is normally carried out at about the reflux temperature of the solvent used. In general, temperatures ranging from about 80° C. to about 150° C. depending, of course, on the solvent (e.g. benzene, toluene, xylene) are used.

The crown-ether-alkali metal complexes can be preformed or can be formed in situ. For ease of operation, it is generally advantageous to form the complexes in situ, and to use an excess of alkali metal hydroxide in order to accelerate the reaction. The preformed complexes are prepared by reacting the appropriate base, e.g. potassium hydroxide, and the appropriate crown ether in methanol or benzene. The methanol or benzene is then removed and toluene or benzene added to the residue.

The hydrolysis product is recovered by adjusting the pH of an aqueous solution of the hydrolysis product to pH from about 0 to about 6.0. Mineral acids, and especially hydrochloric acid, are generally used for reasons of economy. Of course, when the hydrolysis is conducted in a non-aqueous solvent system, the solid hydrolysis product is separated by an appropriate method (filtration, centrifugation) from the solvent system and is then taken up in water prior to pH adjustment. The favored pH range is from about 1 to about 4; the preferred range is from about pH 2 to pH 3.

As noted above, 3,4-dihydro-2-methyl-4-oxo-2H-1,2-benzothiazine-3-carboxylic acid-1,1-dioxide is a valuable intermediate for preparation of N-(2-pyridyl)- and N-(2-thiazolyl)-3,4-dihydro-2-methyl-4-oxo-2H-1,2-benzothiazine-3-carboxamide-1,1-dioxides, both of which are efficient antiinflammatory agents. These compounds are prepared by acylating the appropriate amine ($R_2NH_2$); i.e., 2-aminopyridine or 2-aminothiazole, with a reactive functional derivative of the carboxy group of 3,4-dihydro-2-methyl-4-oxo-2H-1,2-benzothiazine-3-carboxylic acid-1,1-dioxide. Suitable reactive functional derivatives of the acid reactant are the acid chloride, the acid bromide, the acid azide, active esters or thio esters with N-hydroxysuccinimide, N-hydroxyphthalimide, a phenol or thiophenol, reactive intermediates formed with various dehydrative "coupling" agents such as N,N'-dicyclohexylcarbodiimide, N,N'-carbonyldiimidazole, N,N'-carbonylditriazole, N-ethoxycarbonyl-2-ethoxy-1,2-dihydroquinoline, an alkoxyacetylene or hexahalocyclotriphosphatriazines, and mixed anhydrides with alkoxycarbonic acids (especially with those having from one to four carbon atoms in the alkoxy groups) or benzyloxycarbonic acid.

The preferred acetylating agents are the acid chloride and mixed anhydrides because of their ease of preparation.

The acylation is conducted in aqueous or non-aqueous solvent systems. In aqueous systems, the reaction is generally carried out at a pH of from about 6 to about 9 and a temperature of from about 0° C. to about 50° C. It can, when using the acid chloride, also be performed in unstable emulsions of water and a water-immiscible organic solvent such as methyl isobutyl ketone and lower alkyl acetates over the pH range of from about 2 to about 4. When using a carbodiimide in an aqueous system, the pH is desirably adjusted to the range of about 5 to about 8, and preferably to about 6 to 7. In a typical procedure, the acid reactant and carbodiimide are mixed in equimolar proportions in a suitable solvent (tetrahydrofuran, dioxan) and a water-water-miscible organic solvent solution (water plus dioxan or tetrahydrofuran) containing the amine is added at room temperature and the mixture stirred for several hours until reaction is complete. Temperatures of from about −5° C. to 30° C. are generally used. In most instances, an excess up to about 10% of the condensing agent is used. The acylation product is recovered by methods known to the art.

When the acid chloride is used as acylating agent, an acid acceptor, desirably an organic base such as triethylamine, pyridine, N-methylaniline, or an excess of the amine reactant ($R_2NH_2$) or an inorganic base such as sodium carbonate or bicarbonate, is used.

EXAMPLE 1

3,4-Dihydro-2-methyl-4-oxo-2H-1,2-benzothiazine-3-carboxylic Acid-1,1-dioxide (Hydrolysis in Aqueous Medium)

Methyl 3,4-dihydro-2-methyl-4-oxo-2H-1,2-benzothiazine-3-carboxylate-1,1-dioxide (50 g.) is added to a solution of sodium hydroxide (160 g.) in water (500 ml.) at 70° C. The resulting lemon-yellow slurry is then heated at 90°–95° C. for 45 minutes and then cooled to room temperature is an ice-water bath. The pH of the reaction mixture is adjusted to 1–1.5 by gradual addition of concentrated hydrochloric acid (350 ml.). Ice chips are added as necessary to keep the temperature below 35° C. The acid product precipitates and is granulated by stirring at 10°–15° C. for 15 minutes. It is recovered by suction filtration, washed with water (100 ml.) and reslurried in water (250 ml.) for a half hour to remove excess hydrochloric acid. It is again filtered with suction and washed with water (100 ml.). Twenty-five grams of the wet filter cake (total wet filter cake is 25.5 g.) is dissolved in warm methanol (150 ml.), the solution filtered and water (50 ml.) added to the filtrate. The addition of seed crystals causes immediate precipitation of product. The slurry is granulated by stirring at about 10° C. for a half hour. The white crystalline product is separated by filtration, washed with water and air-dried. Yield = 13.2 g., M.p. 144°–146° C.

Evaporation of the filtrate to half-volume affords additional product (3.2 g.). A third crop is recovered by repetition of this procedure (2.6 g.).

Total yield = 16.4 g. (34.6%).

MS (mol.ion) = 255.

IR (KBr): 3535 cm$^{-1}$ (enolic OH), 2900–2000 cm$^{-1}$ (acid OH), 1660 cm$^{-1}$ (C=O), 1340, 1170 cm$^{-1}$ (SO$_2$).

Repetition of this procedure but using potassium hydroxide, lithium hydroxide, calcium hydroxide, magnesium hydroxide or barium hydroxide as base affords similar results.

EXAMPLE 2

3,4-Dihydro-2-methyl-4-oxo-2H-1,2-benzothiazine-3-carboxylic Acid-1,1-Dioxide Hydrolysis in Non-Aqueous Medium (Crown Ether Method)

To a mechanically stirred mixture of potassium hydroxide (2.8 g.), methyl 3,4-dihydro-2-methyl-4-oxo-2H-1,2-benzothiazine-3-carboxylate-1,1-dioxide (6.73 g.) and benzene (100 ml.) is added a solution of dicyclohexyl-18-crown-6 ether (0.93 g.) in benzene (10 ml.) over a period of one minute. The reaction mixture is then heated at reflux for two hours. Additional potassium hydroxide (2.8 g. is then added and refluxing continued for a total of 50 hours. The yellow-brown slurry is filtered while hot, and the filter cake washed with benzene (50 ml.) and dried. It is then dissolved in water (100 ml.) and the solution adjusted to pH 1.0 with hydrochloric acid while maintaining the temperature at about 15° C. The resulting precipitate is granulated for a half-hour, filtered, washed with water and dried (4.4 g. of crude product).

The crude product is dissolved in warm methanol (49 ml.), the solution filtered and then diluted by slow addition of water (63 ml.). The precipitate which forms is granulated for a half-hour at 10°–15° C. and is then filtered, washed with water (2 × 10 ml.) and dried in air. Yield = 3.5 g., 61.9%. M.p., 134°–141° C.

Repetition of this procedure but using 18-crown-6, dibenzo-18-crown-6, cyclohexyl-18-crown-6, cyclohexyl-15-crown-5 and sodium or potassium hydroxides; lithium hydroxide and dibenzo-14-crown-4; barium or strontium hyroxides and binaphthyl-20-crown-6, or calcium hydroxide and dibenzo-30-crown-10 affords the acid.

EXAMPLE 3

Following the procedures of Examples 1 or 2, the esters tabulated below are hydrolyzed to 3,4-dihydro-2-methyl-4-oxo-2H-1,2-benzothiazine-3-carboxyic acid-1,1-dioxide.

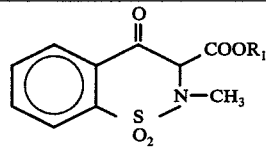

| R$_1$ | Method of Example |
|---|---|
| C$_2$H$_5$ | 1 |
| t-C$_4$H$_9$ | 2 |
| n-C$_8$H$_{17}$ | 1 |
| n-C$_8$H$_{17}$ | 2 |
| n-C$_{12}$H$_{25}$ | 1 |
| n-C$_{12}$H$_{25}$ | 2 |
| C$_6$H$_5$CH$_2$ | 1 |
| C$_6$H$_5$(CH$_2$)$_3$ | 1 |
| C$_6$H$_5$(CH$_2$)$_2$ | 2 |

EXAMPLE 4

N-(2-Pyridyl)-3,4-dihydro-2-methyl-4-oxo-2H-1,2-benzothiazine-3-Carboxamide-1,1-dioxide A 25 ml. three-neck, round-bottom flask equipped with magnetic stirrer, reflux condenser and glass stoppers is charged with thionyl chloride (1.82 ml.), isopropyl ether (12.8 ml.) and 3,4-dihydro-2-methyl-4-oxo-2H-1,2-benzothiazine-3-carboxylic acid-1,1-dioxide (1.28 g.). The mixture is heated at reflux and stirred for five hours and is then evaporated under reduced pressure. The residue is taken up in N,N-dimethylformamide (10 ml.) and the resulting solution used directly in the following step.

To the N,N-dimethylformamide solution of the acid chloride formed above is added, with stirring, 2-aminopyridine (1.03 g.). An exothermic reaction occurs with development of a red color which changes to orange-yellow within about five minutes. The reaction mixture is stirred overnight and is then diluted by slow addition of water (40 ml.). The resulting precipitate is granulated for one-half hour and is then filtered, washed with water and air-dried (1.3 g., 79%). M.p. 160°–175° C. It is purified by dissolution in N,N-dimethylacetamide (1 ml. per 0.1 g.) at 50°–60° C. and precipitation therefrom by addition of a five-fold volume of methanol and chilling. Yield of pure product = 30%; M.p. 198°–200° C. The identity of the compound is confirmed by infrared and mass spectrometry.

A similar result is achieved by substitution of thionyl bromide for thionyl chloride.

EXAMPLE 5

N-(2-Thiazolyl)-3,4-dihydro-2-methyl-4-oxo-2H-1,2-benzothiazine-3-carboxamide-1,1-dioxide The procedure of Example 4 is repeated but using 510 mg. of 3,4-dihydro-2-methyl-4-oxo-2H-1,2-benzothiazine-3-carboxylic acid-1,1-dioxide, 1.45 ml. of thionyl chloride, 10.0 ml. of isopropyl ether and 2.0 ml. of N,N-dimethylformamide to prepare the acid chloride of 3,4-dihydro-2-methyl-4-oxo-2H-1,2-benzothiazine-3-carboxylic acid-1,1-dioxide.

The acid chloride is then reacted with 2-aminothiazole (400 mg.) according to the acylation procedure of Example 4 to afford 532 mg. (79%, crude) of the title product.

It is purified by dissolution in N,N-dimethylacetamide (3 ml.) at 60° C., filtration of the solution followed by dilution of the filtrate with methanol (15 ml.) to precipitate the product. Yield = 208 mg. (33%). M.p. 234°–240° C. Repetition of this treatment affords the pure product.

The identity of the product is confirmed by infrared and mass spectrometry.

EXAMPLE 6

N-(2-Pyridyl)-3,4-dihydro-2-methyl-4-oxo-2H-1,2-benzothiazine-3-carboxamide-1,1-dioxide To a solution of 3,4-dihydro-2-methyl-4-oxo-2H-1,2-benzothiazine-3-carboxylic acid-1,1-dioxide (127 mg.) and 2-aminopyridine (52 mg.) in tetrahydrofuran (5 ml.) is added, with stirring, a solution of N-ethoxycarbonyl-2-ethoxy-1,2-dihydroquinoline (148 mg.) in tetrahydrofuran (1 ml.). The mixture is stirred at room temperature (23°–25° C.) for four hours and is then concentrated under reduced pressure to an oil. Thin layer chromatography on silica gel plates in the system - benzene:acetic acid (95:5) and visualization of the plate under a 366 mµ lamp showed, by comparison with an authentic sample, the title compound is present.

Repetition of this procedure but using N,N'-dicyclohexylcarbodiimide, N,N'-carbonyl-s-triazine, N,N-carbonyldiimidazole, ethoxyacetylene, diphenyl-ketene p-tolylamine, N-hydroxysuccinimide, succinimide, N-hydroxyphthalimide or N-hydroxypiperidine as coupling agents in place of N-ethoxycarbonyl-2-ethoxy-1,2-dihydroquinoline achieves similar results.

What is claimed is:
1. Crystalline 3,4-dihydro-2-methyl-4-oxo-2H-1,2-benzothiazine-3-carboxylic acid-1,1-dioxide.

* * * * *